US00PP11955P2

(12) United States Plant Patent
Bradford

(10) Patent No.: US PP11,955 P2
(45) Date of Patent: Jun. 26, 2001

(54) NECTARINE TREE NAMED 'GRAND CANDY'

(76) Inventor: Lowell Glen Bradford, 12439 E. Savana Rd., Le Grand, CA (US) 95333

( * ) Notice: Subject to any disclaimer, the term of this patent is extended or adjusted under 35 U.S.C. 154(b) by 0 days.

(21) Appl. No.: 09/472,605

(22) Filed: Dec. 27, 1999

(51) Int. Cl.[7] ..... A01H 5/00
(52) U.S. Cl. ..... Plt./190
(58) Field of Search ..... Plt./190

(56) References Cited

U.S. PATENT DOCUMENTS

P.P. 7,918 7/1992 Bradford et al. ..... Plt./192
P.P. 9,961 7/1997 Bradford et al. ..... Plt./190

*Primary Examiner*—Bruce R. Campell
*Assistant Examiner*—Wendy A Baker

(57) ABSTRACT

The present invention relates to a nectarine tree, *Prunus persica,* and more particularly to a new and distinct variety broadly characterized by a medium sized, vigorous, self-fertile, productive and regular bearing tree. The fruit matures under the ecological conditions described approximately the third week in July, with first picking on Jul. 4, 1998. The fruit is uniformly large in size, subacidic and sweet in flavor, globose in shape, clingstone in type, firm and crisp in texture, and fully red in skin color. The variety was a first generation cross using Ruby Diamond (U.S. Plant Pat. No. 7,918) nectarine as the selected seed parent and an unnamed seedling as the selected pollen parent.

1 Drawing Sheet

BACKGROUND OF THE VARIETY

In a continuing effort to improve the quality of fresh market and shipping fruits, I, the inventor, typically hybridize a large number of nectarine and peach seedlings each year. The present invention relates to a new and distinct variety of nectarine tree (*Prunus persica*), which has been denominated varietally as 'GRAND CANDY'. The present variety was hybridized in 1992, grown as a seedling on its own root in the greenhouse, and transplanted to a cultivated area of my experimental orchard at Bradford Farms near Le Grand, Calif. in Merced County (San Joaquin Valley). It was developed as a first generation cross using Ruby Diamond (U.S. Plant Pat. No. 7,918) nectarine as the selected seed parent and an unnamed nectarine as the selected pollen parent. Subsequent to origination of the present variety of nectarine tree, I asexually reproduced it by budding and grafting, in the experimental orchard described above, and such reproduction of plant and fruit characteristics were true to the original plant in all respects. The reproduction of the variety included the use of Nemaguard Rootstock (unpatented), the standard of the stone fruit industry in central California, upon which the present variety was compatible and true to type.

The present variety is most similar to Fire Sweet (U.S. Plant Pat. No. 9,961) nectarine, by producing fruit that is full red in skin color, yellow in flesh color, clingstone in type, subacidic and sweet in flavor, and firm in texture, but is distinguished therefrom and an improvement thereon by having globose instead of reniform glands and by producing fruit that matures about ten days earlier and that has less red streaking in the flesh.

The present variety is similar to its seed parent, Ruby Diamond (U.S. Plant Pat. No. 7,918) nectarine, by producing firm, full red, yellow flesh, nectarines, but is distinguished therefrom by producing fruit that is clingstone instead of freestone in type, that is subacidic instead of acidic in flavor, and that matures about twelve days later.

DRAWING

The accompanying photograph exhibits four whole fruits positioned to display the characteristics of the skin color and form, one fruit divided transversely to the suture plane to reveal the flesh and stone, and typical leaves.

POMOLOGICAL CHARACTERISTICS

Referring now more sepcifically to the pomological characteristics of this new and distinct variety of nectarine tree, the following has been observed of a 6 year-old tree grown under the ecological conditions prevailing near Le Grand, Merced County (San Joaquin Valley), Calif., and was developed at the state of hard shipping ripe on Jul. 20, 1998. All major color code designations are by reference to the Inter-Society Color Council, National Bureau of Standards.

TREE

Size: Medium, reaching and maintaining a height of 11' [3.35 meters] after the 6th growing season utilizing typical dormant pruning.

Vigor: Vigorous, responding typically to irrigation and fertilization. The plant should be grown on a standard commercial rootstock for production purposes. The variety grows about 3' [0.91 meters] of surplus top-growth during the spring and summer.

Growth: Spreading and dense.

Form: Vase formed.

Hardiness: Hardy with respect to typical central California winters.

Production: Very productive, thinning required.

Fertility: Self-fertile.

Bearing: Regular bearer, with no alternate bearing observed.

Trunk:

*Size.*—Medium, reaching a maximum diameter of 6" [152 mm.] after 6 growing seasons.

*Texture.*—Rough.

*Bark color.*—Grayish yellowish brown [80. gy.yBr].

*Lenticels.*—Numerous. Color: Deep orange yellow [69. deep OY]. Typical Size: 3/16" to 3/8" [4.8–9.5 mm.].

Branches:

*Size.*—Medium, typical of *Prunus persica.*

*Color.*—1st Year Wood Topside: Light grayish red [18. l.gy.R]. 1st Year Wood Underside: Brilliant yellow green [116. brill.YG]. Older Wood: Deep yellowish brown [75. deep yBr].

*Texture.*—Smooth on 1st year wood, increasing roughness with age.

*Lenticels.*—Numerous. Color: Light orange yellow [70. l.OY]. Size: 1/8" to 1/4" [3.2–6.4 mm.].

Leaves:

*Size.*—Medium. Average Length: 5" [127.0 mm.]. Average Width: 1½" [38.1 mm.].

*Thickness.*—Medium.

*Form.*—Elliptical.

*Apex.*—Acuminate.

*Base.*—Acute.

*Surface.*—Smooth.

*Color.*—Dorsal Surface: Moderate olive green [125. m.OlG]. Ventral Surface: Moderate yellow green [120. m.YG].

*Margin.*—Finely serrate.

*Venation.*—Pinnately net veined.

*Petiole.*—Average Length: ½" [12.7 mm.]. Average Thickness: 1/16" [1.6 mm.]. Color: Light yellow green [119. l.YG].

*Stipules.*—2 per leaf bud, up to 6 at the growing tip. Average Length: 3/8" [9.5 mm.].

*Glands.*—Numbers: 2 to 3 per leaf. Position: Alternately positioned on petiole and base of blade. Size: Medium. Form: Globose. Color: Light yellow green [119. l.YG].

Flower buds:

*Hardiness.*—Hardy with respect to central California winters.

*Diameter.*—Typically 3/8" [9.5 mm.] 1 week before bloom.

*Length.*—Typically ¾"[19.1 mm.] 1 week before bloom.

*Form.*—Not appressed.

*Color.*—Brilliant purplish pink [246. brill, p. Pk.].

*Surface.*—Pubescent.

Flowers: Perfect, complete, perigynous, usually a single pistil, typically thirty or more stamens, five sepals and petal locations alternately positioned.

*Blooming period.*—Medium as compared with other varieties.

*Onset of bloom.*—One percent on Mar. 4, 1998.

*Duration of bloom.*—One to two weeks, dependent on ambient temperature.

*Type.*—Showy.

*Number of petals.*—Usually five, some doubles.

*Number per cluster.*—Generally from 1 to 3.

*Petal shape.*—Rounded.

*Petal margin.*—Slightly wavy.

*Average petal diameter.*—¾" [19.1 mm.].

*Petal color.*—Pale purplish pink [252. p.pPk].

*Anther color.*—Dark red [16. d.R] when first opened.

*Average pistil length.*—13/16" [20.6 mm.].

*Fragrance.*—Strong when nectar is present.

*Average diameter.*—1⅞" [47.6 mm.].

FRUIT

Maturity when described: hard shipping ripe, Jul. 20, 1998.

Date of first picking: Jul. 14, 1998.

Date of last picking: Jul. 23, 1998.

Size: Uniform, large.

*Average diameter axially.*—2⅝" [66.7 mm.].

*Average diameter across suture plane.*—2⅞" [73.0 mm.].

*Typical weight.*—6.88 ounces [195 grams].

Form: Globose, uniform, mostly symmetrical.

*Longitudinal section form.*—Round.

*Transverse section through diameter.*—Round.

Suture: A shallow groove from the stem along the lateral surface becoming more pronounced toward the apex with a depression beyond the pistil point.

Ventral surface: Rounded.

Lips: Slightly unequal usually, but often equal.

Cavity: Flaring, circular, suture showing on one side, stem markings typical on both sides of the shoulder.

*Depth.*—½" [12.7 mm.].

*Breadth.*—1⅛" [25.7 mm.].

Base: Truncate.

Apex: Rounded.

Pistil point: Oblique, very short in length, depressed within the suture.

Stem: Medium.

*Average length.*—3/8" [9.5 mm.].

*Average width.*—3/16" [4.8 mm.].

Skin:

*Thickness.*—Medium.

*Texture.*—Medium.

*Tenacity.*—Tenacious to flesh.

*Tendency to crack.*—None observed.

*Color.*—Dark red [16. d.R] smoothly blending into a strong reddish orange [35. s.rO] background, brilliant orange yellow [67. brill.OY] stem markings on both sides of the shoulder, and some strong orange yellow [68. s.OY] freckling toward the apex.

Flesh:

*Color.*—Brilliant orange yellow [67. brill.OY] with the slightest amount of moderate red [15. m.R] flecking usually closer to the stone.

*Surface of pit cavity.*—Brilliant yellow [83. brill.Y] with a tinge of moderate red [15. m.R] fibers breaking when twisted away from the stone.

*Amygdalin.*—Scarce.

*Juice.*—Abundant, rich.

*Texture.*—Firm, crisp.

*Fibers.*—Abundant, fine.

*Ripens.*—Earliest at the apex.

*Flavor.*—Subacidic and sweet, typically 15 to 17 brix.

*Aroma.*—Very slight.

*Eating quality.*—Very good.

STONE

Type: Clingstone.

Form: Oval.

Base: Slightly oblique.

Apex: Acute.

Hilum: Narrow.

Sides: Equal.

Surface: Irregularly furrowed throughout, pitted toward the base.

Ridges: Jagged toward the base.

Color: Light brown [57. l.Br] when first removed from fruit.

Pit wall: 1/4" [6.4 mm.] thick.

Tendency to split: None observed.

Kernel:

*Form.*—Oval.

*Taste.*—Bitter.

*Viable.*—Yes.

*Average width.*—9/16" [14.3 mm.].

*Average length.*—¾" [19.1 mm.].

*Pellicle color.*—Grayish brown [61. gy.Br].

*Skin color.*—Pale yellow [89. p.Y] with light brown [57. l.Br] veins when first removed from stone.

*Amygdalin.*—Abundant.

USE

Market: Fresh and long distance shipping.

Keeping quality: Fruit quality observed to remain in good condition in excess of 30 days in cold room at 36° Fahrenheit [2° Celsius].

Resistance to insects: No unusual susceptibilities noted.

Resistance to diseases: No unusual susceptibilities noted.

Although the new variety of nectarine tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of nectarine tree, substantially as illustrated and described, that is most similar to Fire Sweet (U.S. Plant Pat. No. 9,961) nectarine, by producing fruit that is full red in skin color, yellow in flesh color, clingstone in type, subacidic and sweet in flavor, and firm in texture, but is distinguished therefrom and an improvement thereon by having globose instead of reniform glands and by producing fruit that matures about ten days earlier and that has less red streaking in the flesh.

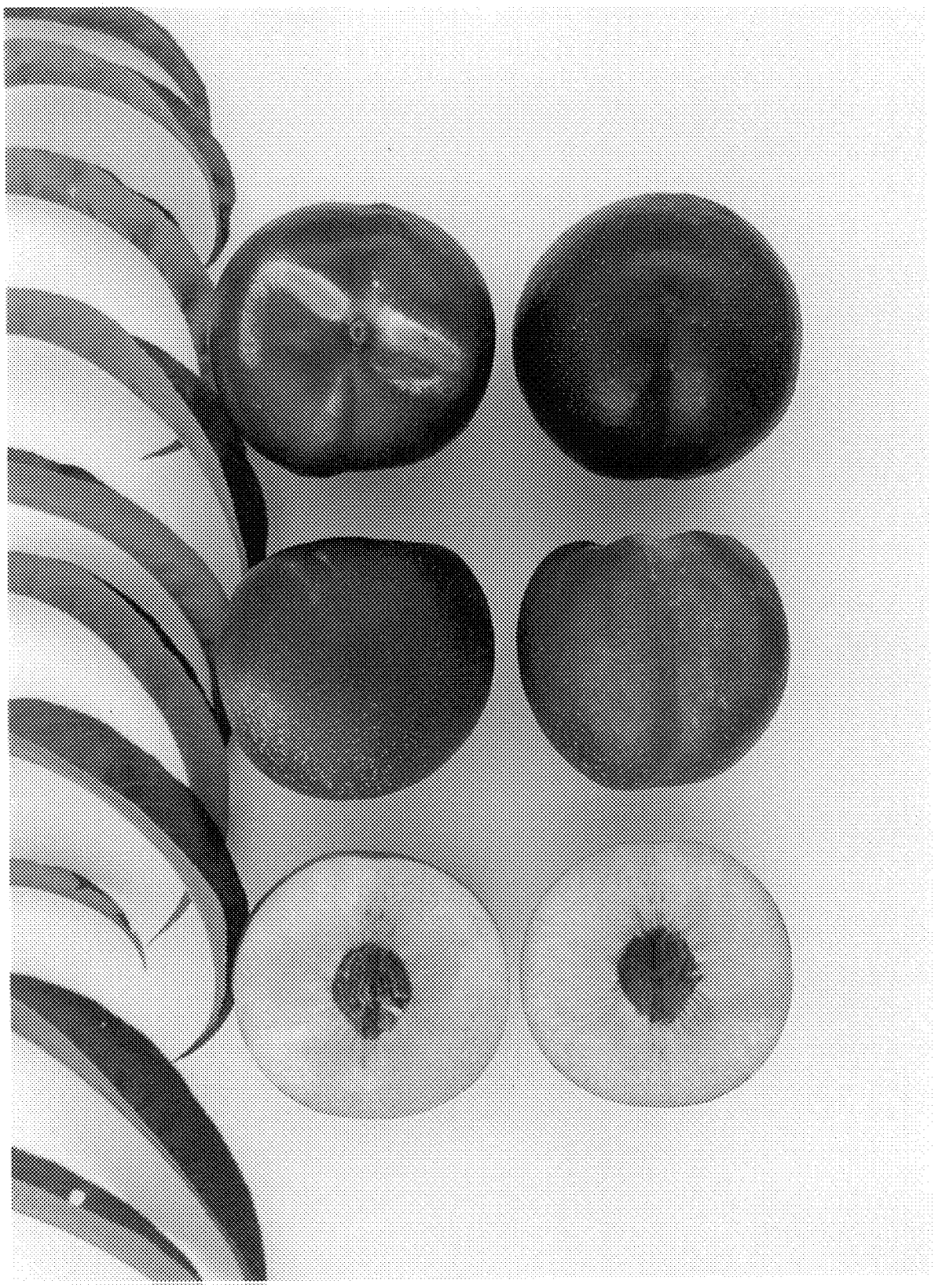

* * * * *